United States Patent
Deshpande et al.

(10) Patent No.: US 11,120,288 B2
(45) Date of Patent: Sep. 14, 2021

(54) EXTENDED PARTICLE SWARM BAND SELECTION

(71) Applicant: ChemImage Corporation, Pittsburgh, PA (US)

(72) Inventors: Shashank R. Deshpande, Pittsburgh, PA (US); Lucas P. Zbur, Indiana, PA (US); Christopher D. Anderson, Pittsburgh, PA (US); Patrick J. Treado, Pittsburgh, PA (US)

(73) Assignee: CHEMIMAGE CORPORATION, Pittsburgh, PA (US)

( * ) Notice: Subject to any disclaimer, the term of this patent is extended or adjusted under 35 U.S.C. 154(b) by 28 days.

(21) Appl. No.: 16/791,634

(22) Filed: Feb. 14, 2020

(65) Prior Publication Data

US 2020/0327349 A1    Oct. 15, 2020

Related U.S. Application Data

(60) Provisional application No. 62/805,742, filed on Feb. 14, 2019.

(51) Int. Cl.
*G06K 9/00* (2006.01)
*B07C 5/00* (2006.01)
*G06K 9/20* (2006.01)
*G06T 7/20* (2017.01)
*G16C 20/20* (2019.01)

(52) U.S. Cl.
CPC ....... *G06K 9/2018* (2013.01); *G06K 9/00134* (2013.01); *G06T 7/20* (2013.01); *G16C 20/20* (2019.02)

(58) Field of Classification Search
USPC ....... 382/100, 103, 106–107, 123, 128, 132, 382/156, 141, 172–173, 181, 199, 209, 382/214, 224, 232, 254, 274, 276, 382/286–291, 305, 312, 191; 209/577; 356/326; 324/207.17
See application file for complete search history.

(56) References Cited

U.S. PATENT DOCUMENTS 6,075,891 A * 6/2000 Burman .................... G06T 7/44
                                                    382/191
6,487,516 B1 * 11/2002 Amorai-Moriya ..........................
                                                G06K 9/00342
                                                    324/207.17

(Continued)

OTHER PUBLICATIONS

Monteiro et al., "Particle Swarms for Feature Extraction of Hyperspectral Data," IEICE Transactions on Information and Systems, vol. E90-D, No. 7 (Jul. 7, 2007) pp. 1038-1046.

*Primary Examiner* — Seyed H Azarian
(74) *Attorney, Agent, or Firm* — Troutman Pepper Hamilton Sanders LLP

(57) ABSTRACT

The disclosure provides methods, systems, and computer program products for detecting compounds of interest that are deposited on or associated with objects of interest. The compounds of interest are not limited and include drugs, alcohol, cannabis, narcotics, controlled substances as defined by state, federal, or international law, ammonium-based explosives, MGE-based explosives, toxic compounds, organic compounds, inorganic compounds, nerve agents, or biological compounds. The disclosure increases the speed and efficiency of processing hyperspectral images, especially on low-power or portable devices.

21 Claims, 5 Drawing Sheets

(56) References Cited

U.S. PATENT DOCUMENTS

| | | | |
|---|---|---|---|
| 6,665,438 B1* | 12/2003 | Lin | G06K 9/0063 |
| | | | 382/191 |
| 8,111,395 B2* | 2/2012 | Lewis | G01J 3/2823 |
| | | | 356/326 |
| 2015/0283586 A1* | 10/2015 | Dante | G06K 9/0063 |
| | | | 209/577 |
| 2017/0090068 A1* | 3/2017 | Xiang | G06F 30/27 |
| 2019/0304168 A1* | 10/2019 | Korb | G06T 15/20 |

* cited by examiner

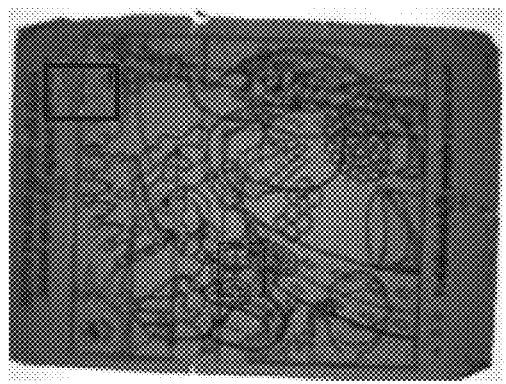 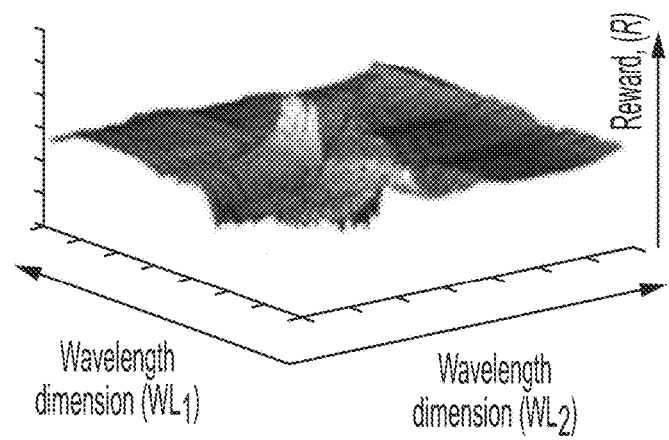
FIG. 3A　　　　　　　　　　FIG. 3B
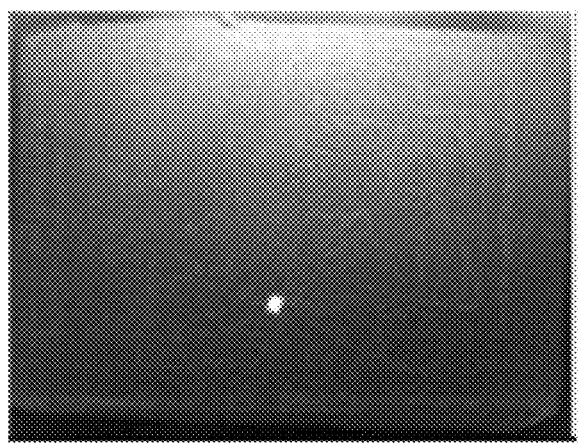 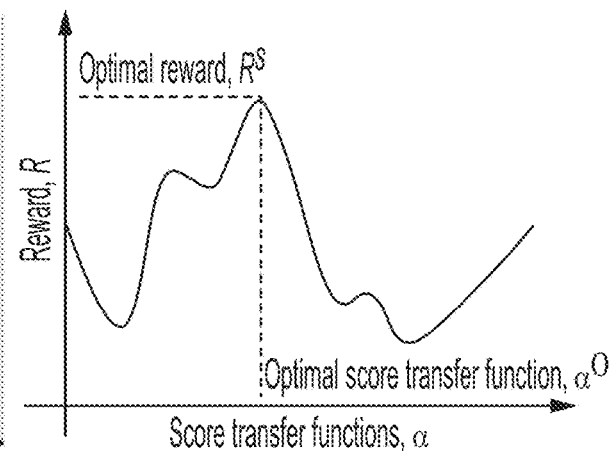
FIG. 3C　　　　　　　　　　FIG. 3D

EXTENDED PARTICLE SWARM BAND SELECTION

CROSS-REFERENCE TO RELATED APPLICATIONS

This application claims priority to U.S. Provisional Patent Application No. 62/805,742 titled "EXTENDED PARTICLE SWARM BAND SELECTION" filed on Feb. 14, 2019, the entire contents of which are incorporated by reference.

FIELD

Hyperspectral imagery is receiving increased attention for non-contact detection of concealed drugs, chemical warfare agents, and explosives. More broadly, hyperspectral imaging is useful for any field where it is desirable to detect distinct chemical compounds or signatures on a material surface, including chemistry, materials science, health care, diagnostics, and manufacturing. However, while hyperspectral images are rich in spectral information content, the sheer amount of dimensional data can be difficult to process. This can be especially challenging for applications that require near real-time or real-time acquisition and/or processing of hyperspectral data on low-power devices or portable devices.

For faster and more efficient processing of hyperspectral images, especially on low-power devices or portable devices, a significant reduction in the number of bands in hyperspectral images is required for object detection with high accuracy. The reduction of the dimensionality of hyperspectral images in remote-sensing hyperspectral images and ground-based hyperspectral images is known as band selection and includes several prior art techniques. Traditionally, transformation-based methods such as Eigenvector analysis, first derivative analysis, and principal component analysis and their variants have been employed for band selection. These methods apply a matrix transformation to the hyperspectral image to project the data onto a lower dimensional coordinate space. In doing so, the transformations lead to the loss of the original spectral information of objects that is often required for subsequent steps in automated target detection algorithms. Furthermore, transformation-based methods require full hyperspectral images to be collected to apply the transformation matrix. This makes real-time or near real-time detection difficult, especially on low-power devices or portable devices.

Alternatively, information-based methods try to measure the information content of each band in a hyperspectral image. The bands with higher information content which have discriminatory capability are then chosen for object detection. Illustrative information-based methods are based on measurements of entropy, mutual information, constrained energy, band correlation, descriptive features, and cluster center distances. One advantage of information-based methods over transformation-based methods is that the band subset retains the original spectral information of the objects of interest. However, information-based methods are highly susceptible to real world external factors that affect the information content, such as environmental changes, illumination variations, noise, etc.

There is a need for techniques that quickly and efficiently obtain optimal score transfer functions for any given chemical or material that is present on an object of interest.

SUMMARY

The disclosure provides methods and systems for detecting compounds of interest that are deposited on or associated with objects of interest.

In one embodiment, there is a system for detecting compounds of interest using hyperspectral imaging, the system comprising a processor which, upon detection of a hyperspectral image collects a hypercube; initializes at least one particle from the hypercube and repeats the following until a combined reward exceeds a threshold for each particle; applies an objective function to the hypercube to determine a reward for each particle; aggregates at least one reward, mutates those particles having lesser rewards to increase the length of the lesser rewards; updates a velocity of each particle, wherein the updated velocity is based on a past velocity position, the current direction of motion of each particle, the individual particle best position, and the global particle best position; and outputs a combined reward to be compared with a threshold for each particle; and outputs an image of a compound of interest if the combined reward exceeds the threshold for each particle.

In another embodiment, the hypercube is imaged by an image detector from wavelengths of electromagnetic radiation that include one or more of about 0.01 nm to about 10 nm (X-ray), about 180 nm to about 380 nm (UV), about 380 nm to about 720 nm (VIS), about 720 nm to about 1100 nm (NIR), about 400 nm to about 1100 nm (VIS-NIR), about 850 nm to about 1800 nm (SWIR), about 1200 nm to about 2450 nm (eSWIR), about 720 nm to about 2500 nm (NIR-eSWIR), about 3 µm to about 8 µm (MWIR), about 8 µm to about 15 µm (LWIR), about 15 µm to about 1 mm (FIR), about 720 nm to about 1 mm (IR), or about 100 µm to about 1 mm (terahertz), combinations of adjacent contiguous ranges thereof, combinations of overlapping ranges thereof, or combinations of ranges thereof that do not overlap.

In another embodiment, the compounds of interest are one or more of drugs, alcohol, cannabis, narcotics, ammonium-based explosives, MGE-based explosives, toxic compounds, organic compounds, inorganic compounds, nerve agents, biological compounds, and combinations thereof.

In another embodiment, the drugs are selected from the group consisting of suboxone, heroin, methamphetamine, methadone, cocaine, ketamine, PCP, acetyl fentanyl, fentanyl citrate, D-amphetamine, lidocaine, cocaine freebase, caffeine, and combinations thereof.

In another embodiment, the ammonium-based explosives are selected from the group consisting of ammonium sulfate, ammonium nitrate fuel oil (ANFO), dynamite, and dyno AP, and combinations thereof.

In another embodiment, the MGE-based explosives are selected from the group consisting of TNT, HMX Octol, RDX, C4, Comp B, and combinations thereof.

In another embodiment, the particle is initialized from a band size of about 1 nm to about 20 nm.

In one embodiment, there is a method for detecting compounds of interest using hyperspectral imaging, the method comprising collecting a hypercube from an image detector; initializing at least one particle from the hypercube and repeating the following until a combined reward exceeds a threshold for each particle; applying an objective function to the hypercube to determine a reward for each particle; aggregating at least one reward, mutating those particles having lesser rewards to increase the length of the lesser rewards; updating the velocity of each particle, wherein the updated velocity is based on a past velocity position, the current direction of motion of each particle, the individual particle best position, and the global particle best position; and outputting a combined reward to be compared with a threshold for each particle; and outputting an image of a compound of interest if the combined reward exceeds the threshold for each particle.

In another embodiment, the hypercube is imaged by an image detector from wavelengths of electromagnetic radiation that include one or more of about 0.01 nm to about 10 nm (X-ray), about 180 nm to about 380 nm (UV), about 380 nm to about 720 nm (VIS), about 720 nm to about 1100 nm (NIR), about 400 nm to about 1100 nm (VIS-NIR), about 850 nm to about 1800 nm (SWIR), about 1200 nm to about 2450 nm (eSWIR), about 720 nm to about 2500 nm (NIR-eSWIR), about 3 μm to about 8 μm (MWIR), about 8 μm to about 15 μm (LWIR), about 15 μm to about 1 mm (FIR), about 720 nm to about 1 mm (IR), or about 100 μm to about 1 mm (terahertz), combinations of adjacent contiguous ranges thereof, combinations of overlapping ranges thereof, or combinations of ranges thereof that do not overlap.

In another embodiment, the compounds of interest are one or more of drugs, alcohol, cannabis, narcotics, ammonium-based explosives, MGE-based explosives, toxic compounds, organic compounds, inorganic compounds, nerve agents, biological compounds, and combinations thereof.

In another embodiment, the drugs are selected from the group consisting of suboxone, heroin, methamphetamine, methadone, cocaine, ketamine, PCP, acetyl fentanyl, fentanyl citrate, D-amphetamine, lidocaine, cocaine freebase, caffeine, and combinations thereof.

In another embodiment, the ammonium-based explosives are selected from the group consisting of ammonium sulfate, ammonium nitrate fuel oil (ANFO), dynamite, and dyno AP, and combinations thereof.

In another embodiment, the MGE-based explosives are selected from the group consisting of TNT, HMX Octol, RDX, C4, Comp B, and combinations thereof.

In another embodiment, the particle is initialized from a band size of about 1 nm to about 20 nm.

In one embodiment, there is computer program product for detecting compounds of interest using hyperspectral imaging, the computer program product comprising a computer readable storage medium having program instruction embodied therewith, the program instructions executable by a processor to cause the processor to collect a hypercube; initialize at least one particle from the hypercube and repeat the following until a combined reward exceeds a threshold for each particle; apply an objective function to the hypercube to determine a reward for each particle; aggregate at least one reward, mutate those particles having lesser rewards to increase the length of the lesser rewards; update a velocity of each particle, wherein the updated velocity is based on a past velocity position, the current direction of motion of each particle, the individual particle best position, and the global particle best position; and output a combined reward to be compared with a threshold for each particle; and output an image of a compound of interest if the combined reward exceeds the threshold for each particle.

In another embodiment, the hypercube is imaged by an image detector from wavelengths of electromagnetic radiation that include one or more of about 0.01 nm to about 10 nm (X-ray), about 180 nm to about 380 nm (UV), about 380 nm to about 720 nm (VIS), about 720 nm to about 1100 nm (NIR), about 400 nm to about 1100 nm (VIS-NIR), about 850 nm to about 1800 nm (SWIR), about 1200 nm to about 2450 nm (eSWIR), about 720 nm to about 2500 nm (NIR-eSWIR), about 3 μm to about 8 μm (MWIR), about 8 μm to about 15 μm (LWIR), about 15 μm to about 1 mm (FIR), about 720 nm to about 1 mm (IR), or about 100 μm to about 1 mm (terahertz), combinations of adjacent contiguous ranges thereof, combinations of overlapping ranges thereof, or combinations of ranges thereof that do not overlap.

In another embodiment, the compounds of interest are one or more of drugs, alcohol, cannabis, narcotics, ammonium-based explosives, MGE-based explosives, toxic compounds, organic compounds, inorganic compounds, nerve agents, biological compounds, and combinations thereof.

In another embodiment, the drugs are selected from the group consisting of suboxone, heroin, methamphetamine, methadone, cocaine, ketamine, PCP, acetyl fentanyl, fentanyl citrate, D-amphetamine, lidocaine, cocaine freebase, caffeine, and combinations thereof.

In another embodiment, the ammonium-based explosives are selected from the group consisting of ammonium sulfate, ammonium nitrate fuel oil (ANFO), dynamite, and dyno AP, and combinations thereof.

In another embodiment, the MGE-based explosives are selected from the group consisting of TNT, HMX Octol, RDX, C4, Comp B, and combinations thereof.

In another embodiment, the particle is initialized from a band size of about 1 nm to about 20 nm.

BRIEF DESCRIPTION OF THE DRAWINGS

Aspects, features, benefits and advantages of the embodiments described herein will be apparent with regard to the following description, appended claims, and accompanying drawings where:

FIG. 3A is an illustration of compounds of interest on an object of interest.

FIG. 3B depicts the resultant search space N that is created by the exemplary score transfer function $WL_1/WL_2$ when applied to the compounds of interest in FIG. 3A.

FIG. 3C is an optimal score image $S^o$ that is generated by applying score transfer function $\alpha^o$ on the search space N of FIG. 3B.

FIG. 3D is a plot representing the correlation between R' and at.

DETAILED DESCRIPTION

Figure 1:
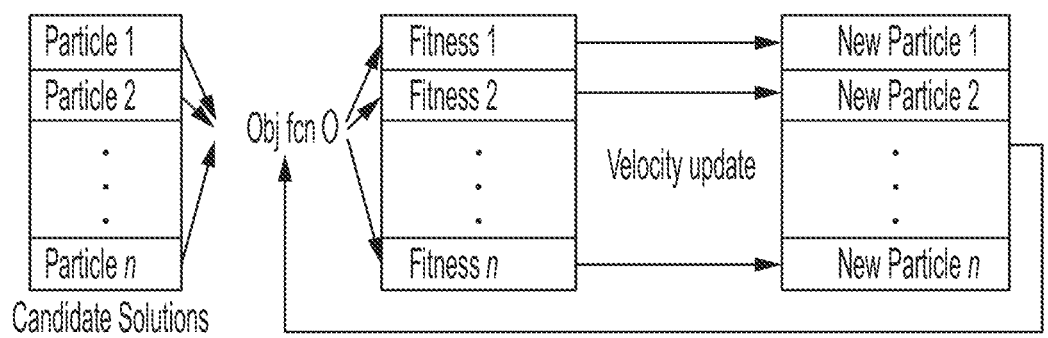
FIG. 1 is an illustration of one embodiment of the Extended Particle Swarm Band Selection (EPSBS) algorithm workflow.

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

As used herein, the term "hypercube" means a multi-band hyperspectral image.

As used herein, the term "score image" means a two-dimensional grayscale image obtained by combining multiple bands via one or more mathematical operations.

As used herein, the term "score transfer function" means a mathematical operation that, when applied to a hypercube, results in a score image. For example, a score transfer function as related to the wavelengths of 1200 nm, 1270 nm, and 1235 nm may be $$Ex - \frac{WL_{1200} + WL_{1270}}{WL_{1235}}.$$

As used herein, the term "particle" or "particles" means a potential solution or potential solutions, respectively, for a score transfer function.

As used herein, the term "length of equation" means the total number of bands plus the total number of operations used in a score transfer function. For example, a length 3 equation may have the structure ($WL_1$ $Op^1$ $WL_2$).

$$Ex - \frac{WL_{1530}}{WL_{1670}}.$$

The disclosure provides systems and methods of detecting compounds of interest that are located on, contacting, or otherwise associated with objects of interest. The systems and methods of the disclosure utilize an extended particle swarm band selection (EPSBS) algorithm to obtain optical score transfer functions for any given compound of interest. The EPSBS algorithm performs simultaneous band selection and operator selection. The EPSBS algorithm maximizes an objective function defined by a product of Modified Fischer's ratio and Z-Scores. The Z-Score measures the signal to noise ratio of the object of interest and background area. The Modified Fisher Ratio measures the relative variance of the object of interest and the background area. The EPSBS algorithm also considers the number of bands required to perform the hyperspectral analysis to be a optimizable parameter, and therefore a mutation step is performed before performing the velocity update. In such a mutation step, particles with lesser rewards are permitted to mutate to match the length of the social best particle in a given iteration.

In one portion of the EPSBS algorithm, the reward of each particle is evaluated using the objective function. Reward evaluation is conducted by supplying the potential solution to the objective function. Individual and global best rewards and positions are updated by comparing the newly evaluated rewards against the previous individual and global best rewards and replacing the best rewards and positions as necessary. The velocity and position update step is responsible for the optimization ability of the EPSBS algorithm. The velocity of each particle in the swarm is updated using the following velocity update rule (terms are defined below in reference to FIGS. 2A and 2B):

$$V^i(t+1)=w*V^i(t)+c1*r1[X^i(t)-x^i(t)]+c2*r2[g(t)-x^i(t)]$$

FIG. 1 is a flowchart of the computation of one portion of the EPSBS algorithm. As shown in FIG. 1, candidate solutions of up to n particles, which form the particle swarm are input into an objective function, which then yields fitness information corresponding to each particle. The velocity update rule is applied to each particle in the swarm, and the solution to the velocity update rule is returned to the objective function. In some embodiments, the steps shown in FIG. 1 may be repeated or iterated 1, 2, 3, 4, 5, 6, 7, 8, 9, or 10 times. However, it is to be understood that the number of iterations is not limited and can be altered based on the compounds of interest, the objects of interest, background environmental factors, and the like.

Figure 2A:
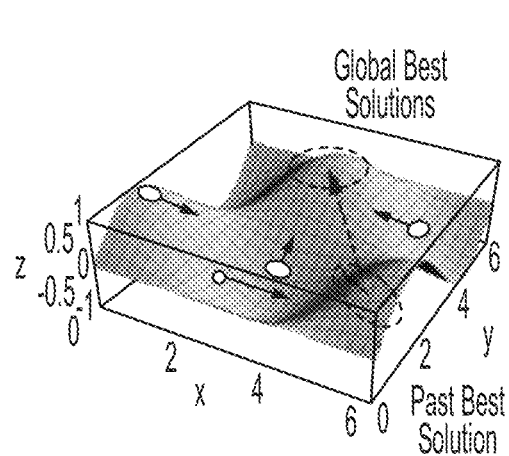
FIGS. 2A and 2B are an illustration of how particles travel through the search space using the velocity update rule.
Figure 2B:
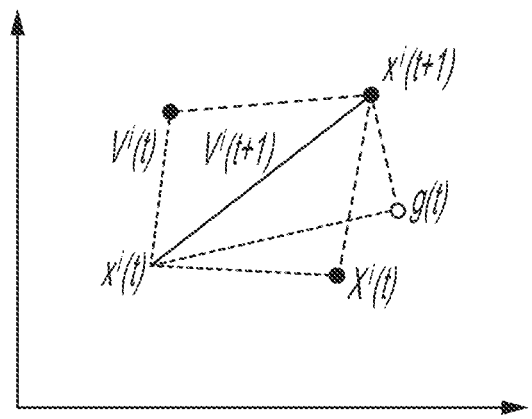

FIGS. 2A and 2B are a graphical depiction of how particles travel through the search space using the velocity update rule. The index of the particle is represented by i. Thus, $V^i(t)$ is the velocity of particle i at iteration t and $x^i(t)$ is the position of particle i at iteration t. Parameter w (inertial chance) regulates the step size of the particle in the current direction of motion, while c1 and c2 regulate the step-size in the direction of individual best and global best, respectively ($0 \leq w \leq 1.2$, $0 \leq c1 \leq 2$, and $0 \leq c2 \leq 2$). The values r1 and r2 ($0 \leq r1 \leq 1$ and $0 \leq r2 \leq 1$) are random values generated for each velocity update. The value Pt) is the individual best candidate solution for particle i at iteration t, and g(t) is the swarm's global best candidate solution at iteration t.

Each of the three terms of the velocity update equation has a different role in the EPSBS algorithm. The first term, $w*V^i(t)$, is the inertia component, which is responsible for moving the particle in the same direction it was originally heading. The second term, $c1*r1[X^i(t)-x^i(t)]$, called the cognitive component, acts as the particle's memory, causing it to tend to return to the regions of the search space in which it has experienced high individual rewards. The third term, $c2*r2[g(t)-x^i(t)]$, called the social component, causes the particle to move to the best region the swarm has found so far. EPSBS-based optimization has been shown to converge quickly to the global optima without getting stuck at local optimum points even when the hypercube search space exceeds 10 dimensions. This ability makes EPSBS-based score transfer function selection a highly reliable approach for generating score images to detect multiple object classes in hyperspectral images.

In the EPSBS algorithm of the disclosure, the above iterations are extended by performing simultaneous band selection and mathematical operator selection in a limited number of iterations. In one embodiment, a hypercube is formed by collecting electromagnetic radiation that is reflected from an object of interest that has an associated compound of interest. Based on the chemical composition of the compound of interest and the chemical composition of the object of interest, among other variables, spatial contrast exists between at least two of the bands that make up the hypercube. The spatial contrast appears between areas of the object of interest that have the compound of interest associated with them and areas of the object of interest that do not have the compound of interest associated with them. Of the collected bands, at least two bands are used to show spatial contrast between the areas of the object of interest that have the associate compound of interest and areas of the object of interest that do not have the compound of interest associated with them.

The EPSBS algorithm is applied to increase the above described spatial contrast. In some embodiments, the score transfer function has a structure of $WL_1/WL_2$, where $WL_1$ is a first wavelength band, and $WL_2$ is a second wavelength band. In an example hypercube collected from the wavelengths of 1000 nm to 1700 nm with a band step size of 5 nm, there are 141 total bands, each of which could potentially correspond to $WL_1$ or $WL_2$. If there is significant contrast between two of the bands, the EPSBS algorithm must resolve which of the 141×140 or 19,740 potential options should be inputted into a score transfer function having a structure of $WL_1/WL_2$. It should be noted, however, that the wavelengths of the hypercube and the band step size are not limited, and that the above ranges are exemplary.

Every possible score transfer function $\alpha^i$ creates a score image $S^i$. A reward is calculated for score image $S^i$ by the equation below:

$$R^i = Z^i * FR^i$$

$$Z^i = \frac{x^T - x^B}{\sigma^B}$$

$$FR^i = \frac{[n^T(x^T - X)^2 + n^B(x^B - X)^2][n^T + n^B - 2]}{([n^T \sigma^{T2} + [n^B \sigma^{B2}])(n^T + n^B - 1)}$$

The correlation between $R^i$ and $\alpha^i$ creates a search space N. The objective of the EPSBS algorithm is to efficiently traverse N to find the optimal transfer function $\alpha^o$ such that the subsequent score image $S^o$ generated using $\alpha^o$ maximizes the reward. For a given class c in the score image $S^i$, $x^T$ and $x^B$ are the mean of T and B, respectively, $\sigma^T$ and $\sigma^B$ are the median absolute deviation of T and B, respectively, $n^T$ and $n^B$ are the number of pixels in T and B, respectively, and X is the mean of T+B.

The above computations and variables are illustrated in FIGS. 3A-3D. In FIG. 3A, the compound of interest is marked in a dashed line square (in the center bottom of the image), while the object of interest is present throughout the image, and presented as the solid line square in the top left of the image. FIG. 3B depicts the resultant search space N that is created by the exemplary score transfer function $WL_1/WL_2$. FIG. 3C is an optimal score image $S^o$ that is generated by applying score transfer function $\alpha^o$ on the search space N. In FIG. 3C, the white spot represents an area of enhanced contrast that indicates the presence of the compound of interest on the object of interest. Finally, FIG. 3D represents the correlation between $R^i$ and $\alpha^i$. In FIG. 3D, the vertical axis corresponds to the value of the reward $R^i$, and the horizontal axis corresponds to the score transfer function $\alpha^i$. The optimal reward $R^o$ represents the point where the highest reward is achieved based on a particular optimal transfer function $\alpha^o$.

While the above formulas and images depicted in FIGS. 3A-3D are examples, the disclosure is not limited to the embodiments depicted therein. For instance, the above description is an example of a length 3 equation because it has two band wavelengths and a single score transfer function. In some embodiments, the equation is a length 4 equation, a length 5 equation, a length 6 equation, a length 7 equation, or a length 8 equation. As can be appreciated by those skilled in the art, increases in equation length result in an exponential increase in the number of possible combinations for the score transfer function.

To avoid the deleterious effects of the exponential increase in the number of possible combinations, the EPSBS algorithm mutates the length of the formulas associated with each particle. To achieve this, the EPSBS algorithm receives the following parameters: Population size, denoted $P_{size}$; length of equation bounds for the search space, denoted $[L_{min}, L_{max}]$, and stopping criteria, which is the minimum acceptable reward $R_s$ that is achieved by a particular proportion of the particle population.

In some embodiments, the minimum acceptable reward $R_s$ is achieved in at least about 10% of the particle population, at least about 20% of the particle population, at least about 30% of the particle population, at least about 40% of the particle population, at least about 50% of the particle population, at least about 60% of the particle population, at least about 70% of the particle population, at least about 80% of the particle population, or at least about 90% of the particle population.

Figure 4:
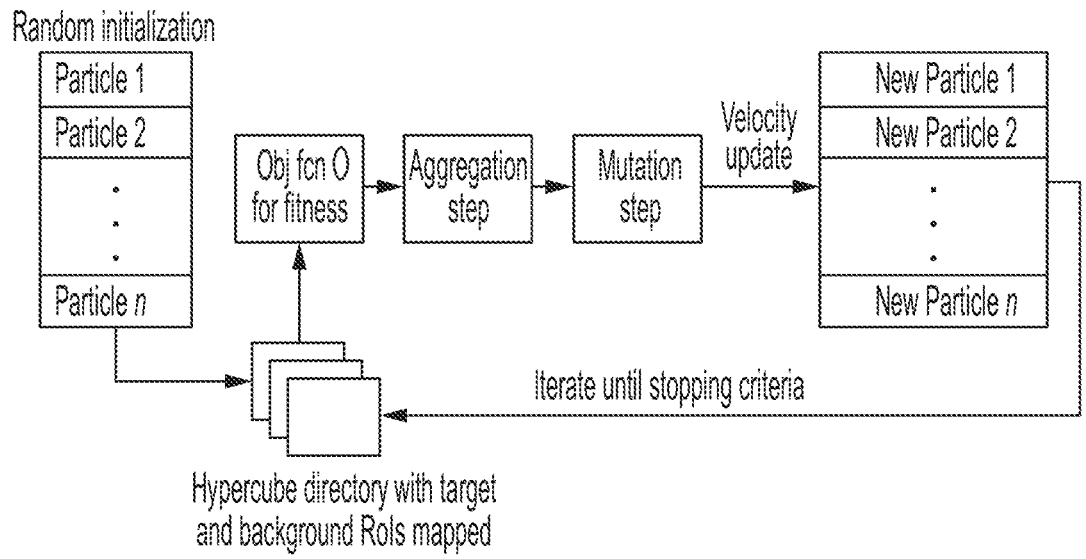
FIG. 4 is an illustration of one embodiment of the EPSBS algorithm workflow.

FIG. 4 is a graphic depiction of the workflow of the EPSBS algorithm. The EPSBS algorithm broadly includes seven steps, which are preparing training data, EPSBS initialization, objective function fitness evaluation, aggregation, mutation, velocity update, and evaluation with termination. The EPSBS algorithm is described in detail below.

First, the training dataset is created. This is achieved by annotating multiple hypercubes [$H_1$ to $H_n$]. In this step, regions of interest are drawn on the hypercubes to mark the material of interest/class and the background of interest. Including multiple hypercubes in the training data increases the robustness of the solution making it invariant to illumination changes and background complexity. Including multiple hypercubes also avoids overfitting. None of the number of hypercubes, the spectra collected in each hypercube, and the size of the bands that make up the hypercube are limited.

The wavelengths of electromagnetic radiation or light that can be imaged by an image detector to form the one or more hypercubes are not limited, and include X-rays, ultraviolet (UV), visible (VIS), near infrared (NIR), visible-near infrared (VIS-NIR), shortwave infrared (SWIR), extended shortwave infrared (eSWIR), near infrared-extended shortwave infrared (NIR-eSWIR), mid-wavelength infrared (MWIR), long-wavelength infrared (LWIR), far-infrared (FIR), infrared (IR), and terahertz radiation. These correspond to wavelengths of about 0.01 nm to about 10 nm (X-ray), about 180 nm to about 380 nm (UV), about 380 nm to about 720 nm (VIS), about 720 nm to about 1100 nm (NIR), about 400 nm to about 1100 nm (VIS-NIR), about 850 nm to about 1800 nm (SWIR), about 1200 nm to about 2450 nm (eSWIR), about 720 nm to about 2500 nm (NIR-eSWIR), about 3 μm to about 8 μm (MWIR), about 8 μm to about 15 μm (LWIR), about 15 μm to about 1 mm (FIR), about 720 nm to about 1 mm (IR), and about 100 μm to about 1 mm (terahertz). The above ranges may be used alone or in combination with any of the other listed ranges. Such combinations include adjacent (contiguous) ranges, overlapping ranges, and ranges that do not overlap. The combination of ranges may be achieved by the inclusion of multiple image detectors, each sensitive to a particular array, or by a single image detector that has a filter array that permits the image detector to sense multiple different ranges.

The band size, and therefore the number of wavelengths for computation by the EPSBS algorithm, is not limited. In some embodiments, the band size is about 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, or a range formed by the combination of one or more of the above values.

Second, the EPSBS algorithm is initialized. In some embodiments, the step of initializing the EPSBS algorithm includes initializing score transfer functions within [$L_{min}$, $L_{max}$]. In some embodiments, the initialization is random. In some embodiments, a user selects the band range to be used for analysis by the EPSBS algorithm, which can be beneficial to limit search space and therefore the required computing resources for implementing the algorithm. The addition of user input to the second step is referred to as adding the priori.

Third, the EPSBS algorithm applies an objective function. An objective function applies $\alpha_i$, i, $\epsilon$, and $P_{size}$ to each of the hypercubes [$H_1$ to $H_n$] to create score images [$S_{i,1}$ to $S_{i,n}$] and calculates reward [$R_{i,1}$ to $R_{i,n}$]. The reward is calculated by the equation below:

$$R^i = Z^i * FR^i$$

$$Z^i = \frac{x^T - x^B}{\sigma^B}$$

$$FR^i = \frac{[n^T(x^T - X)^2 + n^B(x^B - X)^2][n^T + n^B - 2]}{([n^T \sigma^{T2} + [n^B \sigma^{B2}])(n^T + n^B - 1)}$$

where Z is the z-score value and FR is the Modified Fisher Ratio, and a higher reward $R^1$ indicates a higher contrast difference in the score image, and therefore a clearer distinction between the two classes of particles.

Fourth, the aggregation step is performed. Once [$R_{i,1}$ to $R_{i,n}$] is calculated for particle $\alpha_i$, the rewards are combined to obtain a single value, $R_i^T$, and that describes the performance of $\alpha_i$, over [$H_1$ to $H_n$] using the equation below:

$$R_i^T = \min([R_{i,1} \text{ to } R_{i,n}]) + \left[\beta * \frac{1}{1 + \sigma_{[R_{i,1} \text{ to } R_{i,n}]}}\right]$$

where $R_i^T$ is the combined reward, $\sigma_{[R_{i,1} \text{ to } R_{i,n}]}$ is the standard deviation of the distribution [$R_{i,1}$ to $R_{i,n}$], and $\beta$ is the weight for variance.

Fifth, the mutation step is performed. In the mutation step, particles with lesser rewards have a chance to mutate to match the length of the social best particle in a given iteration. This mutation (governed by a mutation probability) is an extremely effective way to combat the combinatorial explosion problem that many search-based band selection methods face. This step allows the particles to avoid getting stuck in the local optima traps and explore search space areas that might have not been previously visible to the algorithm, which results in faster convergence.

In some embodiments, there is a particle $\alpha_i$ in iteration j, with a reward $R_i^T$ and length $l_i$. If $\alpha_{max}$ has $R_{best}^T$, (social best reward for iteration j) and equation length $l_{best}$, $\alpha$, has a chance to mutate to/best with a probability of mutation $P_m$. In such embodiments, the equation that governs mutation is:

$$P_m = \frac{(1-w) + tansig(diff(R_{best}^T, R_i^T))}{2}$$

where w is the value of inertial chance for iteration j.

Figure 5:
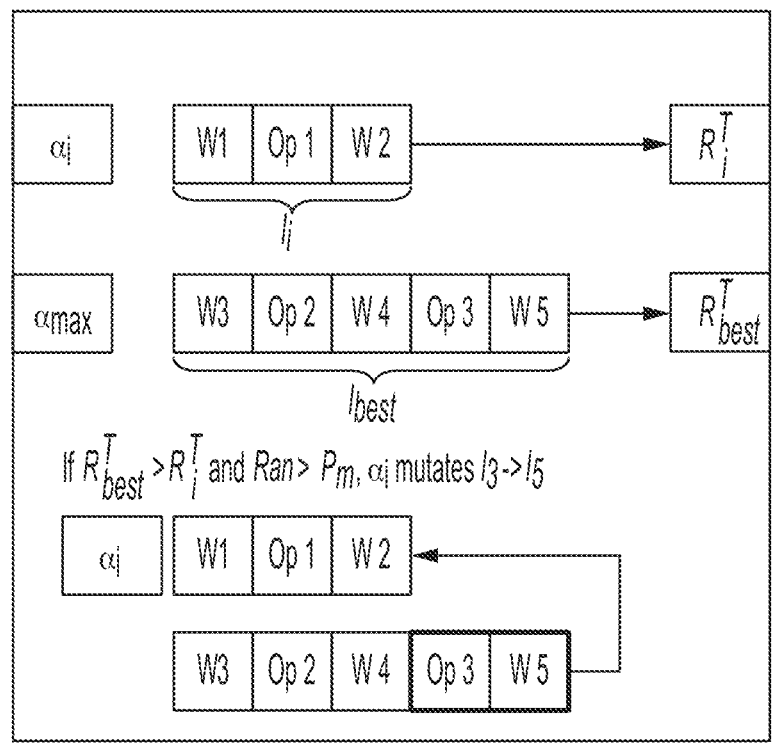
FIG. 5 is an illustration of another embodiment of the EPSBS algorithm workflow.

An illustrative workflow of the mutation step is shown in FIG. 5. In the embodiment shown in FIG. 5, a length 3 equation mutates to a length 5 equation in order to achieve an improved reward. The increased reward indicates greater contrast based on a particular application of the EPSBS algorithm.

Sixth, the velocity update is performed. In the velocity update, the velocity of every particle $\alpha_i$ is calculated, and the velocity of each particle is updated based on its current direction of motion, individual best position and global best position using the equation below:

$$V^i(t+1) = w * V^i(t) + c1 * r1[X^i(t) - x^i(t)] + c2 * r2[g(t) - x^i(t)]$$

In some embodiments, w (which denotes inertial chance) is a linearly increasing variable in each iteration from 0.4 to 1. In the above equation, c1 and c2 are equal to 2. However, these values are not limited and may be altered depending on the compounds of interest, the object of interest, and the like.

Seventh, the step of evaluation is performed. During evaluation, steps 3, 4, 5, and 6 are repeated in order unless or until the stopping criteria $R_s$ is met. Following each iteration, the image is evaluated to determine whether $R_s$ is met. If, after an iteration of steps 3, 4, 5, and 6 is performed, the stopping criteria is not met, a subsequent iteration of the above steps 3, 4, 5, and 6 is performed. If, after an iteration of steps 3, 4, 5, and 6 is performed, the stopping criteria is met, the evaluation terminates the EPSBS algorithm, and the resultant images are outputted.

The objects of interest are not limited and can be any material that is suspected of having compounds of interest on the surface of, concealed within, contacting a surface, mixed with, or otherwise associated with the object of interest. The object of interest may be made of metal, ceramic, paper, plastic, a polymer, concrete, or any combination of one or more of the above materials. In some embodiments, the object of interest is a letter, document, package, parcel, or cargo that is being transported. In some embodiments, the object of interest is a vehicle, automobile, ship, boat, airplane, cargo container, motorcycle, bicycle, train, or combination of one or more of the above.

The compounds of interest are not limited and can include one or more of drugs, alcohol, cannabis, narcotics, controlled substances as defined by state, federal, or international law, ammonium-based explosives, MGE-based explosives, toxic compounds, organic compounds, inorganic compounds, nerve agents, biological compounds, and combinations thereof. Exemplary drugs may include suboxone, heroin, methamphetamine, methadone, cocaine, ketamine, PCP, acetyl fentanyl, fentanyl citrate, D-amphetamine, lidocaine, cocaine freebase, caffeine, and combinations thereof. Exemplary ammonium-based explosives may include ammonium sulfate, ammonium nitrate fuel oil (ANFO), dynamite, and dyno AP, and combinations thereof. Exemplary MGE-based explosives may include TNT, HMX Octol, RDX, C4, Comp B, and combinations thereof.

EXAMPLES

The EPSBS algorithm was tested on Short-Wave Infrared (SWIR) hyperspectral images collected using Multi-Conjugate Filters (MCF). The hyperspectral images contain 141 bands collected discretely from 1000 nm to 1700 nm wavelength with a step size of 5 nm. The Examples simulate two specific scenarios: EXAMPLE 1 Narcotics concealed in mail entering correctional facilities, and EXAMPLE 2 Residue amounts of explosives on real-world substrates in complex backgrounds. These each represent compounds of interest disposed on the surface of objects of interest.

Once the EPSBS algorithm finds the optimal score transfer function, an adaptive thresholding approach is employed to detect the compound of interest. Both the EPSBS algorithm and the detection algorithm are implemented in C#. TABLE 1 lists all the user-defined parameters that were used and their values.

TABLE 1

| Parameter | Value | Definition |
| --- | --- | --- |
| Psize | 2,000 | Population size: number of particles used for exploration. |
| I | 10,000 | Iterations: maximum number of iterations for the algorithm. |
| [Lmin, Lmax] | [3, 11] | Length of equation bounds: bounds for the search space. |
| β | 0.2 | Weight for variance for the reward function. |
| w | Linearly increasing from 0.4 to 1. | Inertial chance in VUR. |
| c1 | 2 | Weight for Individual best directional step-size in VUR. |
| c2 | 2 | Weight for Global best directional step-size in VUR. |

Example 1

To test for drugs concealed in mail, a dataset of 1,000 SWIR images was employed. To simulate mails entering correction facilities, drugs were concealed in a variety of mail articles including envelopes, greeting cards, coloring pages, business cards, and postcards using a variety of concealment methods. Drug concentrations ranged from 5 mg to 20 mg. TABLE 2 lists the compounds including narcotic materials used in the experiment.

TABLE 2

| Material | Number of Samples |
| --- | --- |
| Suboxone | 172 |
| Heroin | 36 |
| Methamphetamine | 54 |
| Methadone | 42 |
| Cocaine | 56 |
| Ketamine/PCP | 48 |
| Acetyl Fentanyl | 36 |
| Fentanyl Citrate | 22 |
| D-Amphetamine | 30 |
| Lidocaine | 36 |
| Cocaine Freebase | 54 |
| Caffeine | 24 |
| Negative control data (Blanks) | 390 |

In the experiments, two different absorption spectra for the listed narcotic materials were observed for suboxone and all of the other drugs listed in TABLE 2. Therefore, it is contemplated that a different score transfer function will be used for suboxone and each of the other drugs.

Four hypercubes were used to train the EPSBS algorithm for finding a Suboxone score transfer function and 20 hypercubes were used to find the other drugs' score transfer function. In the experiments, the transfer function for detecting suboxone was $$\frac{WL_{1200} + WL_{1270}}{WL_{1235}},$$

while the transfer function for detecting the other drugs was $$\frac{WL_{1085} - WL_{1140}}{WL_{1085} + WL_{1140}} * \frac{WL_{1085}}{WL_{1140}}.$$

TABLE 3 lists the detection performance achieved using the EPSBS algorithm described in the specification. As shown by TABLE 3, detection performance was greater than 84% in all instances, with rates as high as 94.11% for other drugs.

TABLE 3

| Material | Probability of Detection (%) | Probability of False Alarms (%) |
| --- | --- | --- |
| Overall | 91.83 | 7.1 |
| Suboxone | 84.88 | 1.16 |
| Other Drugs | 94.11 | 8.33 |

Figure 6:
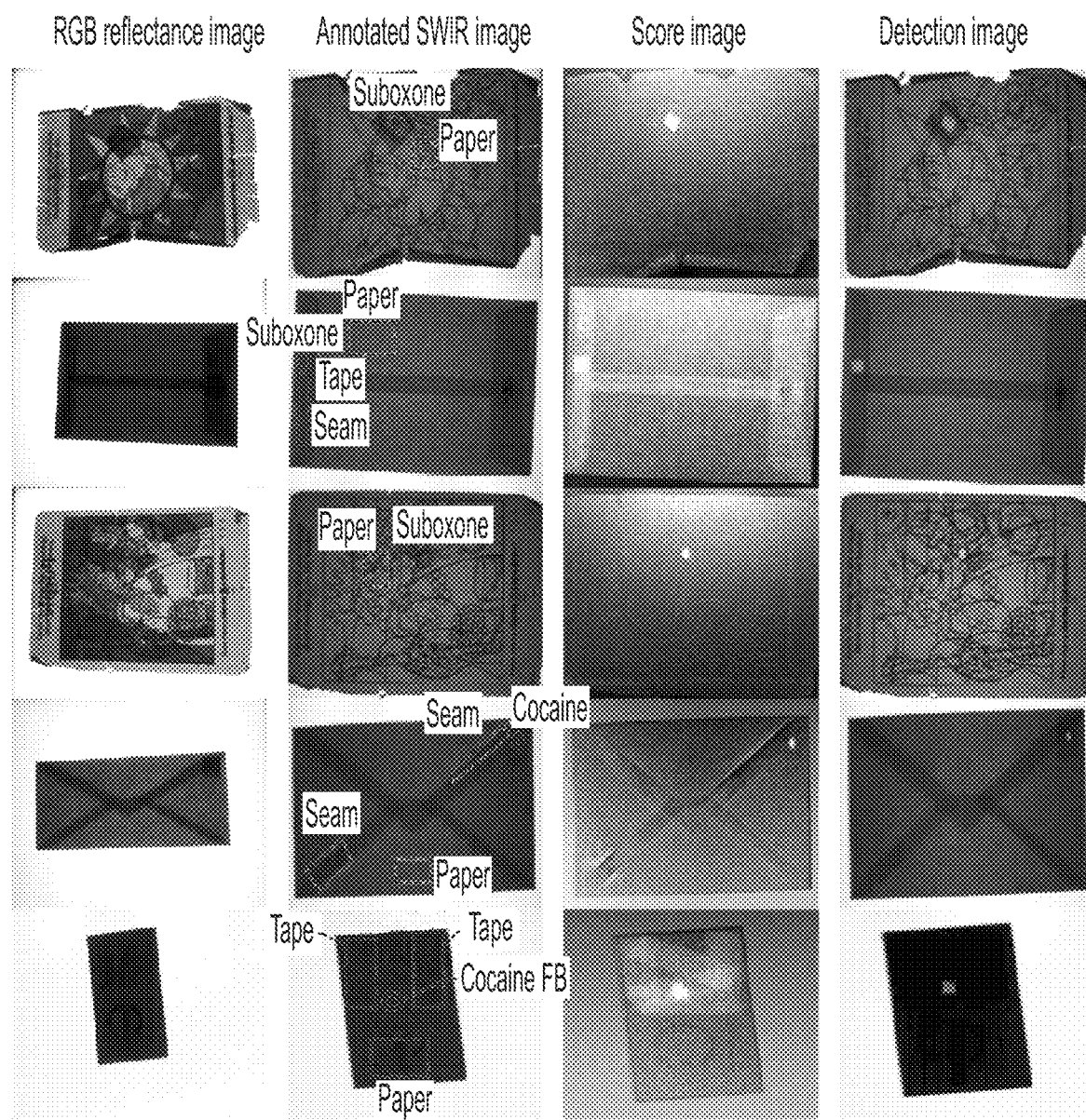
FIG. 6 is an illustration of one embodiment of the disclosure for the detection of drugs.

FIG. 6 depicts the results of band selection using the EPSBS algorithm for detecting narcotic materials concealed in mails entering correctional facilities. In row 1, suboxone is concealed in a coloring page. In row 2, suboxone is concealed in an envelope under glue seams. In row 3, suboxone is concealed in a coloring page. In row 4, cocaine concealed in an envelope under a stamp. In row 5, cocaine freebase is concealed in a business card.

Example 2

To test for explosives as the compound(s) of interest, a dataset of 80 SWIR hyperspectral images was taken. To simulate residue amounts of explosives deposited on real-world substrates in complex backgrounds, small amounts of nine (9) explosives materials, ranging from 250 mg to 1,000 mg in weight each, were deposited on two (2) different car doors. Each of the two car doors had white or red automotive paint, and the car doors represent the objects of interest. The materials were mounted to the doors using plastic covers that covered the explosive material.

Hyperspectral images were collected using SWIR wavelengths and multi-conjugate filters (MCF), with the MCF and image detector located at a standoff distance of 2.5 meters from the car doors. Eight (8) SWIR hypercubes were collected per individual material, and eight (8) hypercubes were collected with all of the explosive materials present in the scene. Based on this experimental configuration, sixteen (16) samples or detection opportunities were available for experimentation.

TABLE 4 lists all the explosive materials used in the Example as compounds of interest. Based on the differing chemical compositions of the explosive materials, the explosive materials were categorized into two distinct groups of compounds of interest. In turn, these two groups yielded two different score transfer functions. Because most of the explosive materials are white in color, confusant materials were introduced along with the explosive materials to ensure the accuracy of the disclosed EPSBS algorithm for explosives detection.

TABLE 4

| Group | Material | Number of samples |
| --- | --- | --- |
| Ammonium based | Ammonium sulfate | 16 |
| | Ammonium nitrate fuel oil (ANFO) | 16 |

TABLE 4-continued

| Group | Material | Number of samples |
|---|---|---|
| | Dynamite | 16 |
| | Dyno AP | 16 |
| MGE | TNT | 16 |
| | HMX Octol | 16 |
| | RDX | 16 |
| | C4 | 16 |
| | Comp B | 16 |
| Confusants | Caffeine | |
| | Urea | |
| | Motor Oil | |
| | Dirt | |
| | Cocaine | |
| | Methamphetamine | |

During testing, four hypercubes containing all of the materials of TABLE 4 were utilized to train the EPSBS algorithm. For ammonium-based explosives, a score transfer function of $$\frac{WL_{1500}}{WL_{1565}}$$

was obtained. For MGE explosives, a score transfer function of $$\frac{WL_{1600} + WL_{1580}}{WL_{1655}}$$

was obtained. TABLE 5 lists the detection performance that was achieved. As shown in TABLE 5, a detection probability of 83.55% overall and a false alarm rate of 8.75% overall were achieved across both ammonium-based and MGE-based explosives. In Example 2, 5 of 141 bands, or about 3.5% of the total number of potential SWIR bands, were required to achieve detection of the listed explosives with high accuracy.

TABLE 5

| Material | Probability of Detection (%) | Probability of False Alarms (%) |
|---|---|---|
| Overall | 83.55 | 8.75 |
| Ammonium based | 82.27 | 2.5 |
| MGE | 84.93 | 6.25 |

Figure 7:
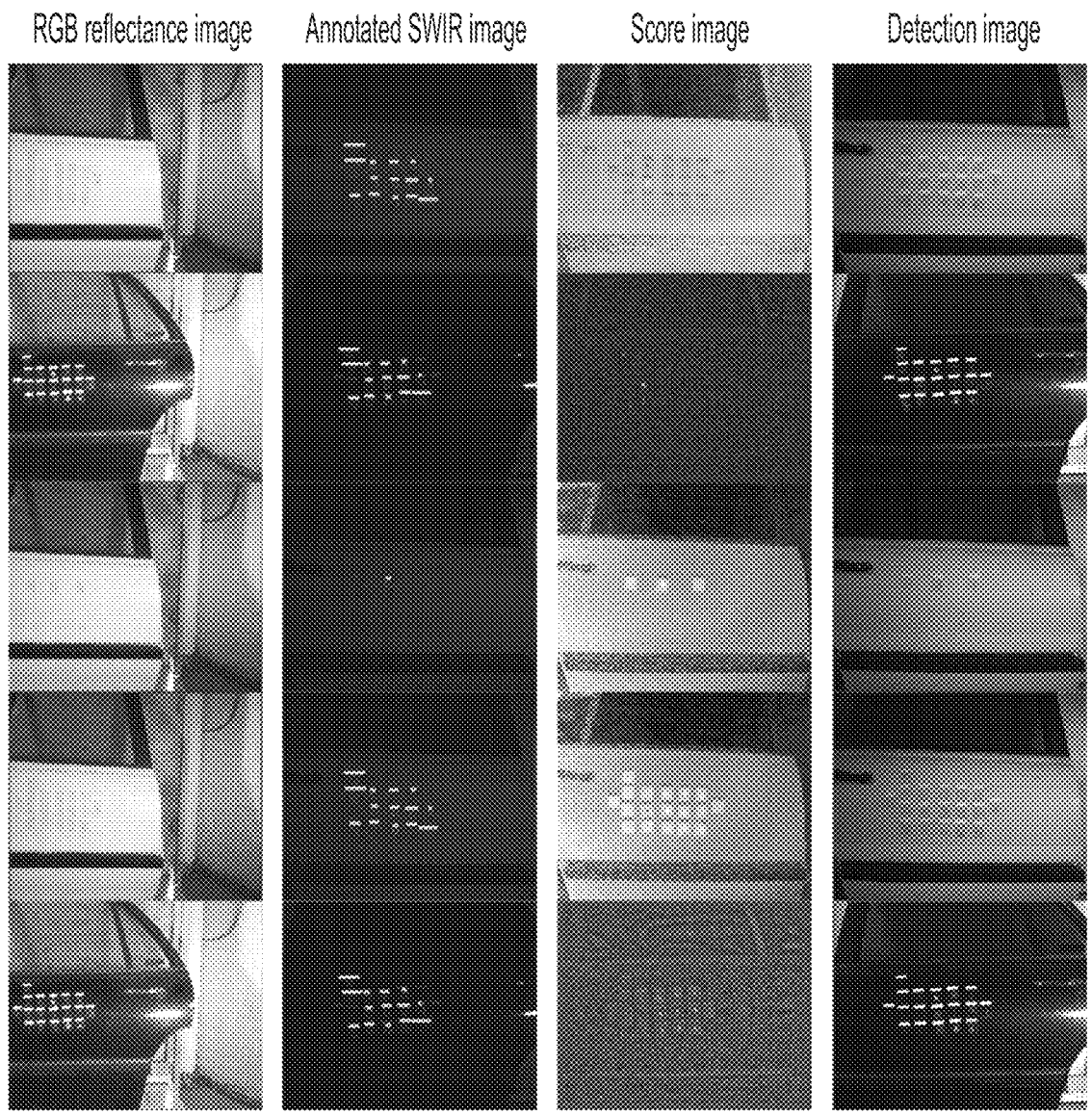
FIG. 7 is an illustration of one embodiment of the disclosure for the detection of explosives.

FIG. 7 depicts the results of band selection using the EPSBS algorithm for detecting explosives materials deposited on real-world substrates in complex backgrounds. Row 1 depicts detecting ammonium-based explosives on a white car door. Row 2 depicts detecting ammonium-based explosives on a red car door. Row 3 depicts detecting TNT on a white car door. Row 4 depicts detecting MGE-based explosives on a white car door. Row 5 depicts detecting MGE-based explosives on a red car door.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present.

For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

The invention claimed is:

1. A system for detecting compounds of interest using hyperspectral imaging, the system comprising:
a processor which, upon detection of a hyperspectral image:
collects a hypercube;
initializes at least one particle from the hypercube and repeats the following until a combined reward exceeds a threshold for each particle;
applies an objective function that is a product of a Modified Fischer's ratio and a Z-Score to the hypercube to calculate a reward for each particle;
aggregates at least one reward,
mutates those particles having lesser rewards to increase the length of the lesser rewards;
updates a velocity of each particle, wherein the updated velocity is based on a past velocity position, the current direction of motion of each particle, the individual particle best position, and the global particle best position; and
outputs a combined reward to be compared with a threshold for each particle; and
outputs an image of a compound of interest if the combined reward exceeds the threshold for each particle.

2. The system of claim 1, wherein the hypercube is imaged by an image detector from wavelengths of electromagnetic radiation that include one or more of about 0.01 nm to about 10 nm (X-ray), about 180 nm to about 380 nm (ultraviolet) (UV), about 380 nm to about 720 nm (visible) (VIS), about 720 nm to about 1100 nm (near infrared) (NIR), about 400 nm to about 1100 nm (visible to near infrared) (VIS-NIR), about 850 nm to about 1800 nm (short wave infrared) (SWIR), about 1200 nm to about 2450 nm (extended shortwave infrared) (eSWIR), about 720 nm to about 2500 nm (near infrared to extended shortwave infrared) (NIR-eSWIR), about 3 μm to about 8 μm (mid-wavelength infrared) (MWIR), about 8 μm to about 15 μm (long-wavelength infrared) (LWIR), about 15 μm to about 1 mm (far infrared) (FIR), about 720 nm to about 1 mm (infrared) (IR), or about 100 μm to about 1 mm (terahertz), combinations of adjacent contiguous ranges thereof, combinations of overlapping ranges thereof, or combinations of ranges thereof that do not overlap.

3. The system of claim 1, wherein the compounds of interest are one or more of drugs, alcohol, cannabis, narcotics, ammonium-based explosives, MGE-based explosives, toxic compounds, organic compounds, inorganic compounds, nerve agents, biological compounds, and combinations thereof.

4. The system of claim 3, wherein the drugs are selected from the group consisting of suboxone, heroin, methamphetamine, methadone, cocaine, ketamine, PCP, acetyl fentanyl, fentanyl citrate, D-amphetamine, lidocaine, cocaine freebase, caffeine, and combinations thereof.

5. The system of claim 3, wherein the ammonium-based explosives are selected from the group consisting of ammonium sulfate, ammonium nitrate fuel oil (ANFO), dynamite, and dyno AP, and combinations thereof.

6. The system of claim 3, wherein the MGE-based explosives are selected from the group consisting of TNT, HMX Octol, RDX, C4, Comp B, and combinations thereof.

7. The system of claim 1, wherein the particle is initialized from a band size of about 1 nm to about 20 nm.

8. The method of claim 1, wherein the particle is initialized from a band size of about 1 nm to about 20 nm.

9. A method for detecting compounds of interest using hyperspectral imaging, the method comprising:
collecting a hypercube from an image detector;
initializing at least one particle from the hypercube and repeating the following until a combined reward exceeds a threshold for each particle;
applying an objective function that is a product of a Modified Fischer's ratio and a Z-Score to the hypercube to calculate a reward for each particle;
aggregating at least one reward,
mutating those particles having lesser rewards to increase the length of the lesser rewards;
updating the velocity of each particle, wherein the updated velocity is based on a past velocity position, the current direction of motion of each particle, the individual particle best position, and the global particle best position; and outputting a combined reward to be compared with a threshold for each particle; and outputting an image of a compound of interest if the combined reward exceeds the threshold for each particle.

10. The method of claim 9, wherein the hypercube is imaged by an image detector from wavelengths of electromagnetic radiation that include one or more of about 0.01 nm to about 10 nm (X-ray), about 180 nm to about 380 nm (ultraviolet) (UV), about 380 nm to about 720 nm (visible) (VIS), about 720 nm to about 1100 nm (near infrared) (NIR), about 400 nm to about 1100 nm (visible to near infrared) (VIS-NIR), about 850 nm to about 1800 nm (short wave infrared) (SWIR), about 1200 nm to about 2450 nm (extended shortwave infrared) (eSWIR), about 720 nm to about 2500 nm (near infrared to extended shortwave infrared) (NIR-eSWIR), about 3 µm to about 8 µm (mid-wavelength infrared) (MWIR), about 8 µm to about 15 µm (long-wavelength infrared) (LWIR), about 15 µm to about 1 mm (far infrared) (FIR), about 720 nm to about 1 mm (infrared) (IR), or about 100 µm to about 1 mm (terahertz), combinations of adjacent contiguous ranges thereof, combinations of overlapping ranges thereof, or combinations of ranges thereof that do not overlap.

11. The method of claim 9, wherein the compounds of interest are one or more of drugs, alcohol, cannabis, narcotics, ammonium-based explosives, MGE-based explosives, toxic compounds, organic compounds, inorganic compounds, nerve agents, biological compounds, and combinations thereof.

12. The method of claim 11, wherein the drugs are selected from the group consisting of suboxone, heroin, methamphetamine, methadone, cocaine, ketamine, PCP, acetyl fentanyl, fentanyl citrate, D-amphetamine, lidocaine, cocaine freebase, caffeine, and combinations thereof.

13. The method of claim 11, wherein the ammonium-based explosives are selected from the group consisting of ammonium sulfate, ammonium nitrate fuel oil (ANFO), dynamite, and dyno AP, and combinations thereof.

14. The method of claim 11, wherein the MGE-based explosives are selected from the group consisting of TNT, HMX Octol, RDX, C4, Comp B, and combinations thereof.

15. A computer program product for detecting compounds of interest using hyperspectral imaging, the computer program product comprising a non-transitory computer readable storage medium having program instruction embodied therewith, the program instructions executable by a processor to cause the processor to:

collect a hypercube;

initialize at least one particle from the hypercube and repeat the following until a combined reward exceeds a threshold for each particle;

apply an objective function that is a product of a Modified Fischer's ratio and a Z-Score to the hypercube to calculate a reward for each particle;

aggregate at least one reward, mutate those particles having lesser rewards to increase the length of the lesser rewards;

update a velocity of each particle, wherein the updated velocity is based on a past velocity position, the current direction of motion of each particle, the individual particle best position, and the global particle best position; and output a combined reward to be compared with a threshold for each particle; and output an image of a compound of interest if the combined reward exceeds the threshold for each particle.

16. The computer program product of claim 15, wherein the hypercube is imaged by an image detector from wavelengths of electromagnetic radiation that include one or more of about 0.01 nm to about 10 nm (X-ray), about 180 nm to about 380 nm (ultraviolet) (UV), about 380 nm to about 720 nm (visible) (VIS), about 720 nm to about 1100 nm (near infrared) (NIR), about 400 nm to about 1100 nm (visible to near infrared) (VIS-NIR), about 850 nm to about 1800 nm (short wave infrared) (SWIR), about 1200 nm to about 2450 nm (extended shortwave infrared) (eSWIR), about 720 nm to about 2500 nm (near infrared to extended shortwave infrared) (NIR-eSWIR), about 3 µm to about 8 µm (mid-wavelength infrared) (MWIR), about 8 µm to about 15 µm (long-wavelength infrared) (LWIR), about 15 µm to about 1 mm (far infrared) (FIR), about 720 nm to about 1 mm (infrared) (IR), or about 100 µm to about 1 mm (terahertz), combinations of adjacent contiguous ranges thereof, combinations of overlapping ranges thereof, or combinations of ranges thereof that do not overlap.

17. The computer program product of claim 15, wherein the compounds of interest are one or more of drugs, alcohol, cannabis, narcotics, ammonium-based explosives, MGE-based explosives, toxic compounds, organic compounds, inorganic compounds, nerve agents, biological compounds, and combinations thereof.

18. The computer program product of claim 17, wherein the drugs are selected from the group consisting of suboxone, heroin, methamphetamine, methadone, cocaine, ketamine, PCP, acetyl fentanyl, fentanyl citrate, D-amphetamine, lidocaine, cocaine freebase, caffeine, and combinations thereof.

19. The computer program product of claim 17, wherein the ammonium-based explosives are selected from the group consisting of ammonium sulfate, ammonium nitrate fuel oil (ANFO), dynamite, and dyno AP, and combinations thereof.

20. The computer program product of claim 17, wherein the MGE-based explosives are selected from the group consisting of TNT, HMX Octol, RDX, C4, Comp B, and combinations thereof.

21. The computer program product of claim 15, wherein the particle is initialized from a band size of about 1 nm to about 20 nm.

* * * * *